(12) United States Patent
Rabinowitz et al.

(10) Patent No.: US 7,087,217 B2
(45) Date of Patent: *Aug. 8, 2006

(54) DELIVERY OF NONSTEROIDAL ANTIINFLAMMATORY DRUGS THROUGH AN INHALATION ROUTE

(75) Inventors: Joshua D. Rabinowitz, Mountain View, CA (US); Alejandro C. Zaffaroni, Atherton, CA (US)

(73) Assignee: Alexza Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/766,279

(22) Filed: Jan. 27, 2004

(65) Prior Publication Data

US 2004/0184996 A1 Sep. 23, 2004

Related U.S. Application Data

(63) Continuation of application No. 10/735,199, filed on Dec. 12, 2003, and a continuation of application No. 10/155,097, filed on May 23, 2002, now Pat. No. 6,716,417.

(60) Provisional application No. 60/317,479, filed on Sep. 5, 2001, provisional application No. 60/294,203, filed on May 24, 2001.

(51) Int. Cl.
*A61K 9/12* (2006.01)
*A61K 9/14* (2006.01)
*A61M 15/00* (2006.01)

(52) U.S. Cl. ........................ 424/45; 424/46; 424/489; 424/499; 514/958; 128/200.14; 128/200.24; 128/203.15

(58) Field of Classification Search .................. 424/45, 424/46, 43, 434, 489, 499; 514/220, 420, 514/958; 128/200.14, 203.15, 200.24
See application file for complete search history.

(56) References Cited

U.S. PATENT DOCUMENTS

| | | | |
|---|---|---|---|
| 3,219,533 A | 11/1965 | Mullins | |
| 3,560,607 A | 2/1971 | Hartley et al. | |
| 3,949,743 A | 4/1976 | Shanbrom | |
| 3,982,095 A | 9/1976 | Robinson | |
| 4,141,369 A | 2/1979 | Burruss | |
| RE30,285 E | 5/1980 | Babington | |
| 4,303,083 A | 12/1981 | Burruss, Jr. | |
| 4,474,191 A | 10/1984 | Steiner | |
| 4,484,576 A | 11/1984 | Albarda | |
| 4,566,451 A | 1/1986 | Badewien | |
| 4,708,151 A | 11/1987 | Shelar | |
| 4,734,560 A | 3/1988 | Bowen | |
| 4,735,217 A | 4/1988 | Gerth et al. | |
| 4,819,665 A | 4/1989 | Roberts et al. | |
| 4,848,374 A | 7/1989 | Chard et al. | |
| 4,853,517 A | 8/1989 | Bowen et al. | |
| 4,895,719 A | 1/1990 | Radhakrishnan et al. | |
| 4,906,417 A | 3/1990 | Gentry | |
| 4,917,119 A | 4/1990 | Potter et al. | |
| 4,924,883 A | 5/1990 | Perfetti et al. | |
| 4,941,483 A | 7/1990 | Ridings et al. | |
| 4,963,289 A | 10/1990 | Ortiz et al. | |
| 5,042,509 A | 8/1991 | Banerjee et al. | |
| 5,049,389 A | 9/1991 | Radhakrishnan | |
| 5,060,671 A | 10/1991 | Counts et al. | |
| 5,099,861 A | 3/1992 | Clearman et al. | |
| 5,135,009 A | 8/1992 | Muller et al. | |
| 5,144,962 A | 9/1992 | Counts et al. | |
| 5,146,915 A | 9/1992 | Montgomery | |
| 5,224,498 A | 7/1993 | Deevi et al. | |
| 5,345,951 A | 9/1994 | Serrano et al. | |
| 5,366,770 A | 11/1994 | Wang | |
| 5,388,574 A | 2/1995 | Ingebrethsen | |
| 5,456,247 A | 10/1995 | Shilling et al. | |
| 5,511,726 A | 4/1996 | Greenspan et al. | |
| 5,544,646 A | 8/1996 | Lloyd et al. | |
| 5,564,442 A | 10/1996 | MacDonald et al. | |
| 5,592,934 A | 1/1997 | Thwaites | |
| 5,605,146 A | 2/1997 | Sarela | |
| 5,649,554 A | 7/1997 | Sprinkel et al. | |
| 5,666,977 A | 9/1997 | Higgins et al. | |
| 5,694,919 A | 12/1997 | Rubsamen et al. | |

(Continued)

FOREIGN PATENT DOCUMENTS

EP 0 358 114 3/1990

(Continued)

OTHER PUBLICATIONS

U.S. Appl. No. 10/633,876, filed Aug. 4, 2003, Hale et al.

(Continued)

*Primary Examiner*—Sreeni Padmanabhan
*Assistant Examiner*—Mina Haghighatian
(74) *Attorney, Agent, or Firm*—Swanson & Bratschum LLC; William L. Leschensky

(57) ABSTRACT

The present invention relates to the delivery of nonsteroidal antiinflammatory drugs (NSAIDs) through an inhalation route. Specifically, it relates to aerosols containing NSAIDs that are used in inhalation therapy. In a method aspect of the present invention, an NSAID is delivered to a patient through an inhalation route. The method comprises: a) heating a coating of an NSAID, on a solid support, to form a vapor; and, b) passing air through the heated vapor to produce aerosol particle having less than 5% NSAID degradation products. In a kit aspect of the present invention, a kit for delivering an NSAID through an inhalation route is provided which comprises: a) a coating of an NSAID composition and b) a device for dispensing said coating as a condensation aerosol.

66 Claims, 1 Drawing Sheet

U.S. PATENT DOCUMENTS

| | | | |
|---|---|---|---|
| 5,724,957 A | 3/1998 | Rubsamen et al. |
| 5,735,263 A | 4/1998 | Rubsamen et al. |
| 5,738,865 A | 4/1998 | Baichwal et al. |
| 5,743,251 A | 4/1998 | Howell et al. |
| 5,758,637 A | 6/1998 | Ivri et al. |
| 5,819,756 A | 10/1998 | Mielordt |
| 5,840,246 A | 11/1998 | Hammons et al. |
| 5,855,913 A | 1/1999 | Hanes et al. |
| 5,874,481 A | 2/1999 | Weers et al. |
| 5,894,841 A | 4/1999 | Voges |
| 5,915,378 A | 6/1999 | Lloyd et al. |
| 5,918,595 A | 7/1999 | Olsson et al. |
| 5,934,272 A | 8/1999 | Lloyd et al. |
| 5,957,124 A | 9/1999 | Lloyd et al. |
| 5,960,792 A | 10/1999 | Lloyd et al. |
| 5,993,805 A | 11/1999 | Sutton et al. |
| 6,041,777 A | 3/2000 | Faithfull et al. |
| 6,051,566 A | 4/2000 | Bianco |
| 6,090,212 A | 7/2000 | Mahawili |
| 6,095,134 A | 8/2000 | Sievers et al. |
| 6,095,153 A | 8/2000 | Kessler et al. |
| 6,102,036 A | 8/2000 | Slutsky et al. |
| 6,131,570 A | 10/2000 | Schuster et al. |
| 6,136,295 A | 10/2000 | Edwards et al. |
| 6,155,268 A | 12/2000 | Takeuchi |
| 6,158,431 A | 12/2000 | Poole |
| 6,234,167 B1 | 5/2001 | Cox et al. |
| 6,241,969 B1 | 6/2001 | Saidi et al. |
| 6,255,334 B1 | 7/2001 | Sands |
| 6,299,900 B1 | 10/2001 | Reed et al. |
| 6,306,431 B1 | 10/2001 | Zhang et al. |
| 6,506,762 B1 | 1/2003 | Horvath et al. |
| 6,514,482 B1 | 2/2003 | Bartus et al. |
| 6,591,839 B1 | 7/2003 | Meyer et al. |
| 6,632,047 B1 | 10/2003 | Vinegar et al. |
| 6,701,922 B1 | 3/2004 | Hindle et al. |
| 6,772,756 B1 | 8/2004 | Shayan |
| 2001/0020147 A1 | 9/2001 | Staniforth et al. |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0086852 A1 | 7/2002 | Cantor |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0000518 A1 | 1/2003 | Rabinowitz et al. |
| 2003/0004142 A1 | 1/2003 | Prior et al. |
| 2003/0005924 A1 | 1/2003 | Rabinowitz et al. |
| 2003/0005925 A1 | 1/2003 | Hale et al. |
| 2003/0007933 A1 | 1/2003 | Rabinowitz et al. |
| 2003/0007934 A1 | 1/2003 | Rabinowitz et al. |
| 2003/0012737 A1 | 1/2003 | Rabinowitz et al. |
| 2003/0012738 A1 | 1/2003 | Rabinowitz et al. |
| 2003/0012740 A1 | 1/2003 | Rabinowitz et al. |
| 2003/0015189 A1 | 1/2003 | Rabinowitz et al. |
| 2003/0015190 A1 | 1/2003 | Rabinowitz et al. |
| 2003/0015196 A1 | 1/2003 | Hodges et al. |
| 2003/0017114 A1 | 1/2003 | Rabinowitz et al. |
| 2003/0017115 A1 | 1/2003 | Rabinowitz et al. |
| 2003/0017116 A1 | 1/2003 | Rabinowitz et al. |
| 2003/0017117 A1 | 1/2003 | Rabinowitz et al. |
| 2003/0017118 A1 | 1/2003 | Rabinowitz et al. |
| 2003/0017119 A1 | 1/2003 | Rabinowitz et al. |
| 2003/0017120 A1 | 1/2003 | Rabinowitz et al. |
| 2003/0021753 A1 | 1/2003 | Rabinowitz et al. |
| 2003/0021754 A1 | 1/2003 | Rabinowitz et al. |
| 2003/0021755 A1 | 1/2003 | Hale et al. |
| 2003/0032638 A1 | 2/2003 | Kim et al. |
| 2003/0035776 A1 | 2/2003 | Hodges et al. |
| 2003/0062042 A1 | 4/2003 | Wensley et al. |
| 2003/0091511 A1 | 5/2003 | Rabinowitz et al. |
| 2003/0138382 A1 | 7/2003 | Rabinowitz |
| 2003/0206869 A1 | 11/2003 | Rabinowitz et al. |
| 2003/0209240 A1 | 11/2003 | Hale et al. |
| 2004/0009128 A1 | 1/2004 | Rabinowitz et al. |
| 2004/0016427 A1 | 1/2004 | Byron et al. |
| 2004/0096402 A1 | 5/2004 | Hodges et al. |
| 2004/0099269 A1 | 5/2004 | Hale et al. |
| 2004/0101481 A1 | 5/2004 | Hale et al. |
| 2004/0105818 A1 | 6/2004 | Hale et al. |
| 2004/0105819 A1 | 6/2004 | Hale et al. |
| 2004/0126326 A1 | 7/2004 | Rabinowitz et al. |
| 2004/0126327 A1 | 7/2004 | Rabinowitz et al. |
| 2004/0126328 A1 | 7/2004 | Rabinowitz et al. |
| 2004/0126329 A1 | 7/2004 | Rabinowitz et al. |
| 2004/0127481 A1 | 7/2004 | Rabinowitz et al. |
| 2004/0127490 A1 | 7/2004 | Rabinowitz et al. |
| 2004/0156788 A1 | 8/2004 | Rabinowitz et al. |
| 2004/0156789 A1 | 8/2004 | Rabinowitz et al. |
| 2004/0156790 A1 | 8/2004 | Rabinowitz et al. |
| 2004/0156791 A1 | 8/2004 | Rabinowitz et al. |

FOREIGN PATENT DOCUMENTS

| | | |
|---|---|---|
| EP | 0 606 486 | 7/1994 |
| EP | 1 080 720 | 7/2001 |
| GB | 502 761 | 3/1939 |
| WO | WO 91/07947 | 6/1991 |
| WO | WO 92/05781 | 4/1992 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/13957 | 3/2001 |
| WO | WO 02/24158 | 3/2002 |
| WO | WO 03/37412 | 5/2003 |

OTHER PUBLICATIONS

U.S. Appl. No. 10/633,877, filed Aug. 4, 2003, Hale et al.
U.S. Appl. No. 10/749,537, filed Dec. 30, 2003, Rabinowitz et al.
U.S. Appl. No. 10/749,539, filed Dec. 30, 2003, Rabinowitz et al.
U.S. Appl. No. 10/766,149, filed Jan. 27, 2004, Rabinowitz et al.
U.S. Appl. No. 10/766,566, filed Jan. 27, 2004, Rabinowitz et al.
U.S. Appl. No. 10/766,574, filed Jan. 27, 2004, Rabinowitz et al.
U.S. Appl. No. 10/766,634, filed Jan. 27, 2004, Rabinowitz et al.

U.S. Appl. No. 10/766,647, filed Jan. 27, 2004, Rabinowitz et al.
U.S. Appl. No. 10/767,115, filed Jan. 28, 2004, Rabinowitz et al.
U.S. Appl. No. 10/768,205, filed Jan. 29, 2004, Rabinowitz et al.
U.S. Appl. No. 10/768,220, filed Jan. 29, 2004, Rabinowitz et al.
U.S. Appl. No. 10/768,281, filed Jan. 29, 2004, Rabinowitz et al.
U.S. Appl. No. 10/768,293, filed Jan. 29, 2004, Rabinowitz et al.
U.S. Appl. No. 10/769,046, filed Jan. 30, 2004, Rabinowitz et al.
U.S. Appl. No. 10/769,051, filed Jan. 30, 2004, Rabinowitz et al.
U.S. Appl. No. 10/769,157, filed Jan. 29, 2004, Rabinowitz et al.
U.S. Appl. No. 10/769,197, filed Jan. 29, 2004, Rabinowitz et al.
U.S. Appl. No. 10/775,583, filed Feb. 9, 2004, Rabinowitz et al.
U.S. Appl. No. 10/775,586, filed Feb. 9, 2004, Rabinowitz et al.
U.S. Appl. No. 10/791,915, filed Mar. 3, 2004, Hale et al.
U.S. Appl. No. 10/792,001, filed Mar. 3, 2004, Rabinowitz et al.
U.S. Appl. No. 10/792,012, filed Mar. 3, 2004, Hale et al.
U.S. Appl. No. 10/792,013, filed Mar. 3, 2004, Rabinowitz et al.
U.S. Appl. No. 10/792,096, filed Mar. 3, 2004, Hale et al.
U.S. Appl. No. 10/792,239, filed Mar. 3, 2004, Hale et al.
U.S. Appl. No. 10/813,721, filed Mar. 31, 2004, Rabinowitz et al.
U.S. Appl. No. 10/813,722, filed Mar. 31, 2004, Rabinowitz et al.
U.S. Appl. No. 10/814,690, filed Mar. 31, 2004, Rabinowitz et al.
U.S. Appl. No. 10/814,998, filed Mar. 31, 2004, Rabinowitz et al.
U.S. Appl. No. 10/815,527, filed Apr. 1, 2004, Rabinowitz et al.
U.S. Appl. No. 10/816,407, filed Apr. 1, 2004, Rabinowitz et al.
U.S. Appl. No. 10/816,492, filed Apr. 1, 2004, Rabinowitz et al.
U.S. Appl. No. 10/816,567, filed Apr. 1, 2004, Rabinowitz et al.
U.S. Appl. No. 10/912,462, filed Aug. 4, 2004, Hale et al.
Bennett, R.L. et al. (1981). "Patient-Controlled Analgesia: A New Concept of Postoperative Pain Relief," *Annual Surg.* 195(6):700-705.
Carroll, M.E. et al. (1990), "Cocaine-base smoking in rhesus monkeys: reinforcing and physiological effects," *Psychopharmacology* (Berl). 102:443-450.
Clark, A. and Byron, P. (1986). "Dependence of Pulmonary Absorption Kinetics on Aerosol Particle Size," *Z. Erkrank.* 166:13-24.
Darquenne, C. et al. (1997). "Aerosol Dispersion in Human Lung: Comparison Between Numerical Simulations and Experiments for Bolus Tests," *American Physiological Society.* 966-974.
Davies, C.N. et al. (May 1972). "Breathing of Half-Micron Aerosols," *Journal of Applied Physiology.* 32(5):591-600.

Dershwitz, M., M.D., et al. (Sep. 2000). "Pharmacokinetics and Pharmacodynamics of Inhaled versus Intravenous Morphine in Healthy Volunteers," *Anesthesiology.* 93(3): 619-628.
Finlay, W.H. (2001). "The Mechanics of Inhaled Pharmaceutical Aerosols", Academic Press: San Diego Formula 2.39. pp. 3-14 (Table of Contents). pp. v-viii.
Gonda,I. (1991). "Particle Deposition in the Human Respiratory Tract," Chapter 176, *The Lung: Scientific Foundations.* Crystal R.G. and West, J.B. (eds.), Raven Publishers, New York. pp. 2289-2294.
Hatsukami D, et al. (May 1990) "A method for delivery of precise doses of smoked cocaine-base to humans." *Pharmacology Biochemistry & Behavior.* 36(1):1-7.
Heyder, J. et al. (1986). "Deposition of Particles in the Human Respiratory Tract in the Size Range 0.005-15 µm," *J. Aerosol Sci.* 17(5):811-822.
Huizer, H., "Analytical studies on illicit heron. V. Efficacy of volatilization during heroin smoking." *Pharmaceutisch Weekblad Scientific Edition* (1987). 9(4):203-211.
Hurt, R.D., MD and Robertson, C.R., PhD, (Oct. 1998). "Prying Open the Door to the Tobacco Industry's Secrets About Nicotine: The Minnesota Tobacco Trial," *JAMA* 280(13):1173-1181.
Lichtman, A.H. et al. (1996). "Inhalation Exposure to Volatilized Opioids Produces Antinociception in Mice," Journal of Pharmacology and Experimental Therapeutics. 279(1):69-76.
Martin, B.R. and Lue, L.P. (May/Jun. 1989). "Pyrolysis and Volatilization of Cocaine," *Journal of Analytical Toxicology* 13:158-162.
Mattox, A.J. and Carroll, M.E., (1996). "Smoked heroin self-administration in rhesus monkeys," *Psychopharmacology,* 125:195-201.
Meng, Y. et al. Inhalation Studies With Drugs of Abuse, *NIDA Research Monograph,* (1997) 173:201-224.
Meng, Y., et al. (1999). "Pharmacological effects of methamphetamine and other stimulants via inhalation exposure," *Drug and Alcohol Dependence.* 53:111-120.
Office Action mailed Aug. 13, 2003 for U.S. Appl. No. 10/153,313 filed May 21, 2002 "Delivery of Benzodiazepines Through an Inhalation Route".
Pankow, J.F. et al. (1997). "Conversion of Nicotine in Tobacco Smoke to Its Volatile and Available Free-Base Form Through the Action of Gaseous Ammonia," *Envron. Sci. Technol.* 31:2428-2433.
Pankow, J. (Mar. 2000). ACS Conference-San Francisco-Mar. 26, 2000. Chemistry of Tobacco Smoke. pp. 1-8.
Seeman, J. et al. (1999). "The Form of Nicotine in Tobacco. Thermal Transfer of Nicotine and Nicotine Acid Salts to Nicotine in the Gas Phase," *J. Agric. Food Chem.* 47(12):5133-5145.
Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271-1280.
Vapotronics, Inc. (1998) located at http://www.vapotronics.com.au/banner.htm., 11 pages, (visited on Jun. 5, 2000).
Ward, M.E. MD, et al. (Dec. 1997). "Morphine Pharmacokinetics after Pulmonary Administration from a Novel Aerosol Delivery System," *Clinical Pharmacology & Therapeutics* 62(6):596-609.
Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior.* 55(2):237-248.
U.S. Appl. No. 10/057,198, filed Oct. 26, 2001, Lloyd et al.
U.S. Appl. No. 10/146,088, filed May 13, 2002, Hale et al.
U.S. Appl. No. 10/280,315, filed Oct. 25, 2002, Shen.
U.S. Appl. No. 10/302,614, filed Nov. 21, 2002, Lu.
U.S. Appl. No. 10/322,227, filed Dec. 17, 2002, Novack et al.
U.S. Appl. No. 10/442,385, filed May 20, 2003, Cross et al.
U.S. Appl. No. 10/719,540, filed Nov. 20, 2003, Hale et al.
U.S. Appl. No. 10/850,895, filed May 20, 2004, Damani et al.
U.S. Appl. No. 10/851,018, filed May 20, 2004, Hale et al.
U.S. Appl. No. 10/851,429, filed May 20, 2004, Hale et al.
U.S. Appl. No. 10/851,432, filed May 20, 2004, Hale et al.
U.S. Appl. No. 10/851,883, filed May 20, 2004, Hale et al.
U.S. Appl. No. 10/861,554, filed Jun. 3, 2004, Cross et al.
U.S. Appl. No. 10/912,417, filed Aug. 4, 2004, Bennett et al.
U.S. Appl. No. 10/917,720, filed Aug. 12, 2004, Hale et al.
U.S. Appl. No. 10/917,735, filed Aug. 12, 2004, Hale et al.
Office Action mailed Dec. 4, 2003 for U.S. Appl. No. 10/057,198 filed Oct. 26, 2001, "Method And Device For Delivering A Physiologically Active Compound".
Office Action mailed Jan. 12, 2005 for U.S. Appl. No. 10/057,197 filed Oct. 26, 2001, "Aerosol Generating Device And Method".
Office Action mailed Jun. 3, 2004 for U.S. Appl. No. 10/057,197 filed Oct. 26, 2001, "Aerosol Generating Device And Method".
Office Action mailed Dec. 15, 2003 for U.S. Appl. No. 10/057,197 filed Oct. 26, 2001, "Aerosol Generating Device And Method".
Office Action mailed Feb. 27, 2004 for U.S. Appl. No. 10/146,080 filed May 13, 2002, "Aerosol Forming Device For Use In Inhalation Therapy".

DELIVERY OF NONSTEROIDAL ANTIINFLAMMATORY DRUGS THROUGH AN INHALATION ROUTE

This application is a continuation of U.S. patent application Ser. Nos. 10/155,097, now U.S. Pat. No. 6,716,417, and 10/735,199, entitled "Delivery of Nonsteroidal Antiinflammatory Drugs Through an Inhalation Route," filed May 23, 2002, and Dec. 12, 2003, respectively, Rabinowitz and Zaffaroni, which claim priority to U.S. provisional application Ser. No. 60/294,203 entitled "Thermal Vapor Delivery of Drugs," filed May 24, 2001, Rabinowitz and Zaffaroni and to U.S. provisional application Ser. No. 60/317,479 entitled "Aerosol Drug Delivery," filed Sep. 5, 2001, Rabinowitz and Zaffaroni, the entire disclosures of which are hereby incorporated by reference.

FIELD OF THE INVENTION

The present invention relates to the delivery of nonsteroidal anti-inflammatory drugs (NSAIDs) through an inhalation route. Specifically, it relates to aerosols containing NSAIDs that are used in inhalation therapy.

BACKGROUND OF THE INVENTION

There are a number of nonsteroidal compositions currently marketed for the treatment of inflammation. The compositions contain at least one active ingredient that provides for observed therapeutic effects. Among the active ingredients given in such antiinflammatory compositions are indomethacin, ketoprofen, celecoxib, rofecoxib, meclofenamic acid, fenoprofen, diflunisal, tolfenamic acid, naproxen, ibuprofen, flurbiprofen, and nabumetone.

It is desirable to provide a new route of administration for nonsteroidal antiinflammatory drugs that rapidly produces peak plasma concentrations of the compounds. The provision of such a route is an object of the present invention.

SUMMARY OF THE INVENTION

The present invention relates to the delivery of nonsteroidal anti-inflammatory drugs (NSAIDs) through an inhalation route. Specifically, it relates to aerosols containing NSAIDs that are used in inhalation therapy.

In a composition aspect of the present invention, the aerosol comprises particles comprising at least 5 percent by weight of an NSAID. Preferably, the particles comprise at least 10 percent by weight of an NSAID. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of an NSAID.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of NSAID degradation products. Preferably, the particles comprise less than 5 percent by weight of NSAID degradation products. More preferably, the particles comprise less than 2.5, 1, 0.5, 0.1 or 0.03 percent by weight of NSAID degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.2.

Typically, the aerosol is formed by heating a composition containing an NSAID to form a vapor and subsequently allowing the vapor to condense into an aerosol.

In another composition aspect of the present invention, the aerosol comprises particles comprising at least 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone. Preferably, the particles comprise at least 10 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products. Preferably, the particles comprise less than 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products. More preferably, the particles comprise less than 2.5, 1, 0.5, 0.1 or 0.03 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol has an inhalable aerosol drug mass density greater than 5 mg/L. Preferably, the aerosol has an inhalable aerosol drug mass density greater than 7.5 mg/L. More preferably, the aerosol has an inhalable aerosol drug mass density greater than 10 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s). In certain embodiments the particles have an MMAD of from about 0.2 to about 3 microns.

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.2.

Typically, the aerosol is formed by heating a composition containing indomethacin, ketoprofen, celecoxib, rofecoxib, meclofenamic acid, fenoprofen, diflunisal, tolfenamic acid, naproxen, ibuprofen, flurbiprofen, or nabumetone to form a vapor and subsequently allowing the vapor to condense into an aerosol.

In a method aspect of the present invention, an NSAID is delivered to a mammal through an inhalation route. The method comprises: a) heating a composition, wherein the composition comprises at least 5 percent by weight of an NSAID, to form a vapor; and, b) allowing the vapor to cool, thereby forming a condensation aerosol comprising particles, which is inhaled by the mammal. Preferably, the composition that is heated comprises at least 10 percent by weight of an NSAID. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an NSAID.

Typically, the particles comprise at least 5 percent by weight of an NSAID. Preferably, the particles comprise at least 10 percent by weight of an NSAID. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an NSAID.

Typically, the aerosol has a mass of at least 10 μg. Preferably, the aerosol has a mass of at least 100 μg. More preferably, the aerosol has a mass of at least 200 μg.

Typically, the particles comprise less than 10 percent by weight of NSAID degradation products. Preferably, the particles comprise less than 5 percent by weight of NSAID degradation products. More preferably, the particles comprise 2.5, 1, 0.5, 0.1 or 0.03 percent by weight of NSAID degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.2.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, the delivered condensation aerosol results in a peak plasma concentration of an NSAID in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

In another method aspect of the present invention, one of indomethacin, ketoprofen, celecoxib, rofecoxib, meclofenamic acid, fenoprofen, diflunisal, tolfenamic acid, naproxen, ibuprofen, flurbiprofen, or nabumetone is delivered to a mammal through an inhalation route. The method comprises: a) heating a composition, wherein the composition comprises at least 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone, to form a vapor; and, b) allowing the vapor to cool, thereby forming a condensation aerosol comprising particles, which is inhaled by the mammal. Preferably, the composition that is heated comprises at least 10 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone.

Typically, the particles comprise at least 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone. Preferably, the particles comprise at least 10 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone.

Typically, the aerosol has a mass of at least 10 μg. Preferably, the aerosol has a mass of at least 100 μg. More preferably, the aerosol has a mass of at least 200 μg.

Typically, the particles comprise less than 10 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products. Preferably, the particles comprise less than 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products. More preferably, the particles comprise 2.5, 1, 0.5, 0.1 or 0.03 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.2.

Typically, the delivered aerosol has an inhalable aerosol drug mass density greater than 5 mg/L. Preferably, the delivered aerosol has an inhalable aerosol drug mass density greater than 7.5 mg/L. More preferably, the delivered aerosol has an inhalable aerosol drug mass density greater than 10 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, greater than 5 mg of indomethacin, ketoprofen, celecoxib, rofecoxib, meclofenamic acid, fenoprofen, diflunisal, tolfenamic acid, naproxen, ibuprofen, flurbiprofen, or nabumetone is delivered to the mammal in a single inspiration. Preferably, greater than 7.5 mg of indomethacin, ketoprofen, celecoxib, rofecoxib, meclofenamic acid, fenoprofen, diflunisal, tolfenamic acid, naproxen, ibuprofen, flurbiprofen, or nabumetone is delivered to the mammal in a single inspiration. More preferably, greater than 10 mg of indomethacin, ketoprofen, celecoxib, rofecoxib, meclofenamic acid, fenoprofen, diflunisal, tolfenamic acid, naproxen, ibuprofen, flurbiprofen, or nabumetone is delivered to the mammal in a single inspiration.

Typically, the delivered condensation aerosol results in a peak plasma concentration of indomethacin, ketoprofen, celecoxib, rofecoxib, meclofenamic acid, fenoprofen, diflunisal, tolfenamic acid, naproxen, ibuprofen, flurbiprofen, or nabumetone in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

In a kit aspect of the present invention, a kit for delivering an NSAID through an inhalation route to a mammal is provided which comprises: a) a composition comprising at least 5 percent by weight of an NSAID; and, b) a device that forms an NSAID drug aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an NSAID.

Typically, the device contained in the kit comprises: a) an element for heating the NSAID composition to form a vapor; b) an element allowing the vapor to cool to form an aerosol; and, c) an element permitting the mammal to inhale the aerosol.

In a kit aspect of the present invention, a kit for delivering indomethacin, ketoprofen, celecoxib, rofecoxib, meclofenamic acid, fenoprofen, diflunisal, tolfenamic acid, naproxen, ibuprofen, flurbiprofen, or nabumetone through an inhalation route to a mammal is provided which comprises: a) a composition comprising at least 5 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone; and, b) a device that forms an indomethacin, ketoprofen, celecoxib, rofecoxib, meclofenamic acid, fenoprofen, diflunisal, tolfenamic acid, naproxen, ibuprofen, flurbiprofen, or nabumetone aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of indomethacin, ketoprofen, celecoxib, rofecoxib, meclofenamic acid, fenoprofen, diflunisal, tolfenamic acid, naproxen, ibuprofen, flurbiprofen, or nabumetone.

Typically, the device contained in the kit comprises: a) an element for heating the indomethacin, ketoprofen, celecoxib, rofecoxib, meclofenamic acid, fenoprofen, diflunisal, tolfenamic acid, naproxen, ibuprofen, flurbiprofen, or nabumetone composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
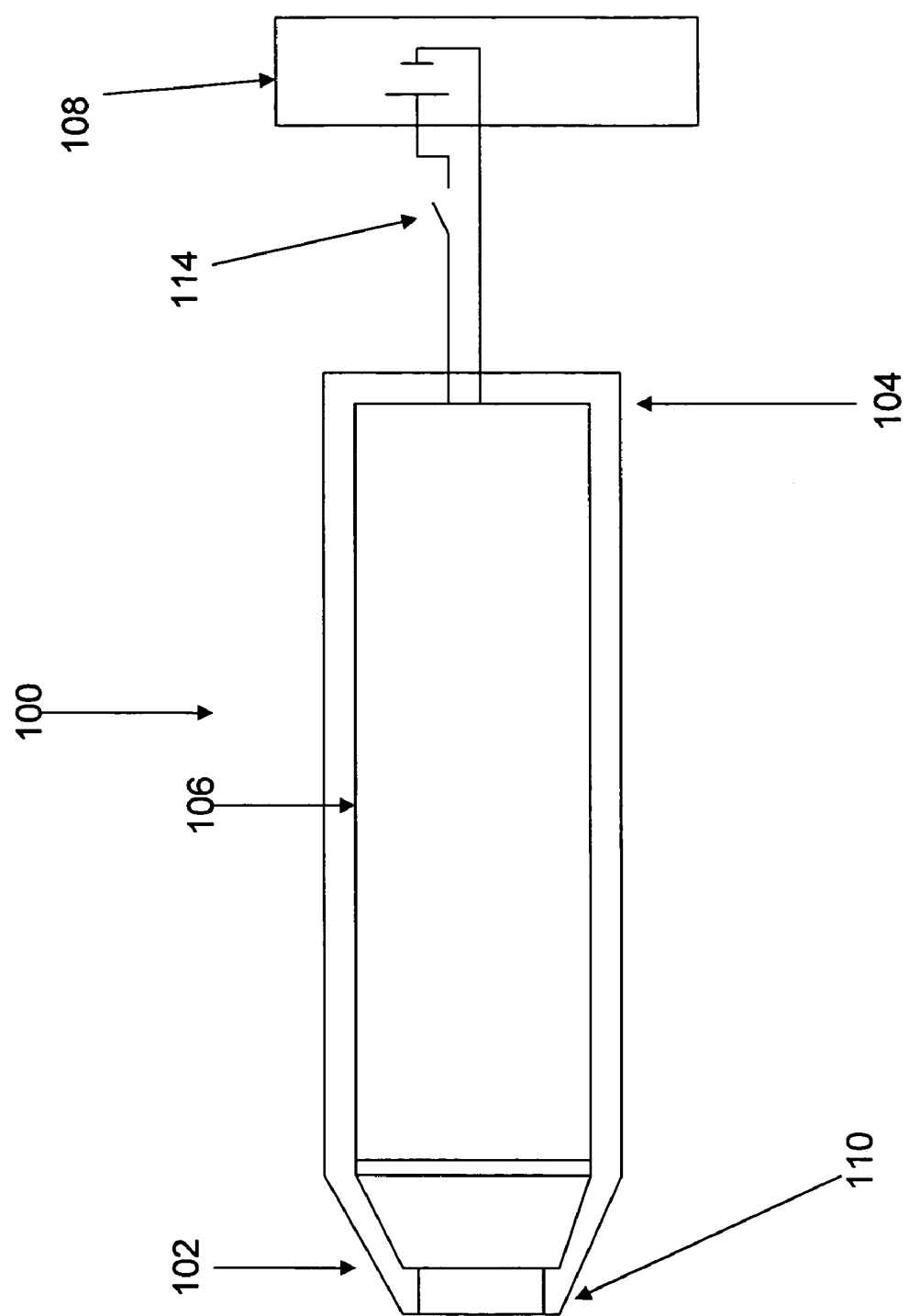
FIG. 1 shows a cross-sectional view of a device used to deliver NSAID aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of NSAID per unit volume of aerosol.

"Aerosol mass density" refers to the mass of particulate matter per unit volume of aerosol.

"Aerosol particle density" refers to the number of particles per unit volume of aerosol.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Celecoxib" refers to 4-[5-(4-methylphenyl)-3-(trifluoromethyl)-1H-pyrazol-1-yl]benzenesulfonamide.

"Celecoxib degradation product" refers to a compound resulting from a chemical modification of celecoxib. The modification, for example, can be the result of a thermally or photochemically induced reaction. Such reactions include, without limitation, oxidation and hydrolysis.

"Condensation aerosol" refers to an aerosol formed by vaporization of a substance followed by condensation of the substance into an aerosol.

"Diflunisal" refers to 2',4'-difluoro-4-hydroxy-[1,1'-biphenyl]-3-carboxylic acid.

"Diflunisal degradation product" refers to a compound resulting from a chemical modification of diflunisal. The modification, for example, can be the result of a thermally or photochemically induced reaction. Such reactions include, without limitation, oxidation and hydrolysis.

"Fenoprofen" refers to α-methyl-3-phenoxy-benzeneacetic acid.

"Fenoprofen degradation product" refers to a compound resulting from a chemical modification of fenoprofen. The modification, for example, can be the result of a thermally or photochemically induced reaction. Such reactions include, without limitation, oxidation and hydrolysis.

"Flurbiprofen" refers to 2-fluoro-α-methyl-[1, 1'-biphenyl]-4-acetic acid.

"Flurbiprofen degradation product" refers to a compound resulting from a chemical modification of flurbiprofen. The modification, for example, can be the result of a thermally or photochemically induced reaction. Such reactions include, without limitation, oxidation and hydrolysis.

"Ibuprofen" refers to α-methyl-4-(2-methyl-propyl)benzene acetic acid.

"Ibuprofen degradation product" refers to a compound resulting from a chemical modification of ibuprofen. The modification, for example, can be the result of a thermally or photochemically induced reaction. Such reactions include, without limitation, oxidation and hydrolysis.

"Indometbacin" refers to 1-(4-chlorobenzoyl)-5-methoxy-2-methyl-1H-indole-3-acetic acid.

"Indomethacin degradation product" refers to a compound resulting from a chemical modification of indomethacin. The modification, for example, can be the result of a thermally or photochemically induced reaction. Such reactions include, without limitation, oxidation and hydrolysis.

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Ketoprofen" refers to 3-benzoyl-α-methyl-benzeneacetic acid.

"Ketoprofen degradation product" refers to a compound resulting from a chemical modification of ketoprofen. The modification, for example, can be the result of a thermally or photochemically induced reaction. Such reactions include, without limitation, oxidation and hydrolysis.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Meclofenamic Acid" refers to 2-[(2,6-dichloro-3-methylphenyl)amino]benzoic acid.

"Meclofenamic acid degradation product" refers to a compound resulting from a chemical modification of meclofenamic acid. The modification, for example, can be the result of a thermally or photochemically induced reaction. Such reactions include, without limitation, oxidation and hydrolysis.

"Nabumetone" refers to 4-(6-methoxy-2-naphthalenyl)-2-butanone.

"Nabumetone degradation product" refers to a compound resulting from a chemical modification of nabumetone. The modification, for example, can be the result of a thermally or photochemically induced reaction. Such reactions include, without limitation, oxidation and hydrolysis.

"Naproxen" refers to (αS)-6-methoxy-α-methyl-2-naphthaleneacetic acid.

"Naproxen degradation product" refers to a compound resulting from a chemical modification of naproxen. The modification, for example, can be the result of a thermally or photochemically induced reaction. Such reactions include, without limitation, oxidation and hydrolysis.

"NSAID degradation product" refers to a compound resulting from a chemical modification of an NSAID. The modification, for example, can be the result of a thermally or photochemically induced reaction. Such reactions include, without limitation, oxidation and hydrolysis.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized NSAID produced by an inhalation device per unit time.

"Rofecoxib" refers to 4-[4-(methylsulfonyl)-phenyl]-3-phenyl-2(5H)-furanone.

"Rofecoxib degradation product" refers to a compound resulting from a chemical modification of rofecoxib. The modification, for example, can be the result of a thermally or photochemically induced reaction. Such reactions include, without limitation, oxidation and hydrolysis.

"Tolfenamic acid" refers to 2-[(3-chloro-2-methylphenyl)amino]benzoic acid.

"Tolfenamic acid degradation product" refers to a compound resulting from a chemical modification of tolfenamic acid. The modification, for example, can be the result of a thermally or photochemically induced reaction. Such reactions include, without limitation, oxidation and hydrolysis.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of NSAID Containing Aerosols

Any suitable method is used to form the aerosols of the present invention. A preferred method, however, involves heating a composition comprising an NSAID to form a vapor, followed by cooling of the vapor such that it condenses to provide an NSAID comprising aerosol (condensation aerosol). The composition is heated in one of four forms: as pure active compound (e.g., pure indomethacin, ketoprofen, celecoxib, rofecoxib, meclofenamic acid, fenoprofen, diflunisal, tolfenamic acid, naproxen, ibuprofen, flurbiprofen, or nabumetone); as a mixture of active compound and a pharmaceutically acceptable excipient; as a salt form of the pure active compound; and, as a mixture of active compound salt form and a pharmaceutically acceptable excipient.

Salt forms of NSAIDs (e.g., indomethacin, ketoprofen, celecoxib, rofecoxib, meclofenamic acid, fenoprofen, diflunisal, tolfenamic acid, naproxen, ibuprofen, flurbiprofen, or nabumetone) are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with the NSAID. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the NSAID compositions is performed using any suitable method. Examples of methods by which heat can be generated include the following: passage of current through an electrical resistance element; absorption of electromagnetic radiation, such as microwave or laser light; and, exothermic chemical reactions, such as exothermic salvation, hydration of pyrophoric materials and oxidation of combustible materials.

Delivery of NSAID Containing Aerosols

NSAID containing aerosols of the present invention are delivered to a mammal using an inhalation device. Where the aerosol is a condensation aerosol, the device has at least three elements: an element for heating an NSAID containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the NSAID containing aerosol is described in reference to FIG. 1. Delivery device 100 has a proximal end 102 and a distal end 104, a heating module 106, a power source 108, and a mouthpiece 110. An NSAID composition is deposited on a surface 112 of heating module 106. Upon activation of a user activated switch 114, power source 108 initiates heating of heating module 106 (e.g, through ignition of combustible fuel or passage of current through a resistive heating element). The NSAID composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of NSAID containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of NSAID Containing Aerosols

The dosage amount of an NSAID in aerosol form is generally no greater than twice the standard dose of the drug given orally; oftentimes, the dose is less than the standard oral dose. (Indomethacin, ketoprofen, celecoxib, rofecoxib, meclofenamic acid, fenoprofen, diflunisal, tolfenamic acid, naproxen, ibuprofen, flurbiprofen, or nabumetone are typically provided at the following strengths for oral administration: 25 mg, 25 to 50 mg, 100 mg, 50 mg, 200 mg, 50 mg, 200 mg, 250 mg, 200 mg, 250 mg, 200 mg, 50 mg, and 500 mg respectively.) A typical dosage of an NSAID aerosol is either administered as a single inhalation or as a series of inhalations taken within an hour or less (dosage equals sum of inhaled amounts). Where the drug is administered as a series of inhalations, a different amount may be delivered in each inhalation.

One can determine the appropriate dose of NSAID containing aerosols to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of NSAID Containing Aerosols

Purity of an NSAID containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of NSAID degradation products.

Particle size distribution of an NSAID containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi$*$D^3$*$\phi$/6, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering an NSAID containing aerosol into a confined chamber via an inhalation device over a set period of time (e.g., 3 s). Where the aerosol is pure NSAID, the amount of drug collected in the chamber is measured as described above. The rate of drug aerosol formation is equal to the amount of NSAID collected in the chamber divided by the duration of the collection time. Where the NSAID containing aerosol comprises a pharmaceutically acceptable excipient, multiplying the rate of aerosol formation by the percentage of NSAID in the aerosol provides the rate of drug aerosol formation.

Utility of NSAID Containing Aerosols

The NSAID containing aerosols of the present invention are typically used for the treatment of inflammation.

The following examples are meant to illustrate, rather than limit, the present invention.

Indomethacin, ketoprofen, meclofenamic acid sodium salt, fenoprofen calcium salt, diflunisal, tolfenamic acid, naproxen, ibuprofen, flurbiprofen, and nabumetone are commercially available from SIGMA (www.sigma-aldrich-.com). Celecoxib and rofecoxib can be isolated using standard methods from CELEBREX® and VIOXX® respectively. Other NSAIDs can be similarly obtained.

EXAMPLE 1

General Procedure for Volatilizing Compounds

A solution of drug in a minimal amount of an appropriate solvent (e.g., dichloromethane or methanol) is coated on a 4.0 cm×7.5 cm piece of aluminum foil (precleaned with acetone). The solvent is allowed to evaporate. The coated foil is wrapped around a 300 watt halogen tube (Feit Electric Company, Pico Rivera, Calif.), which is inserted into a glass tube sealed at one end with a rubber stopper. Running 60 V of alternating current (driven by line power controlled by a variac) through the bulb for 3-18 s affords thermal vapor (including aerosol), which is collected on the glass tube walls. Reverse-phase HPLC analysis with detection by absorption of 225 nm light is used to determine the purity of the aerosol. (When desired, the system is flushed through with argon prior to volatilization.)

NSAID aerosols were obtained in the following purities and amounts using this procedure: indomethacin (99% purity, 0.61 mg); ketoprofen (100% purity, 2.72 mg); celecoxib (100% purity, 10 mg); rofecoxib (97.5% purity, 4.1 mg); meclofenamic acid (100% purity); fenoprofen (100%, 1.61 mg); diflunisal (100%, 5.47 mg); tolfenamic acid (94.2% purity, 6.49 mg); naproxen (100% purity, 4 mg); ibuprofen (100% purity, 1.81 mg); flurbiprofen (100% purity, 4.1 mg); and, nabumetone (100% purity, 4.8 mg).

The invention claimed is:

1. A condensation aerosol for delivery of a drug selected from the group consisting of indomethacin, ketoprofen, celcoxib, rofecoxib, meclofenamic acid, fenoprofen, diflunisal, tolfenamic acid, naproxen, ibuprofen, flurbiprofen and nabumetone, wherein the condensation aerosol is formed by heating a thin layer containing the drug, on a solid support, to produce a vapor of the drug, and condensing the vapor to form a condensation aerosol characterized by less than 10% drug degradation products by weight, and an MMAD of less than 5 microns.

2. The condensation aerosol according to claim 1, wherein the condensation aerosol is formed at a rate greater than $10^9$ particles per second.

3. The condensation aerosol according to claim 2, wherein the condensation aerosol is formed at a rate greater than $10^{10}$ particles per second.

4. A method of producing a drug selected from the group consisting of indomethacin, ketoprofen, celcoxib, rofecoxib, meclofenamic acid, fenoprofen, diflunisal, tolfenamic acid, naproxen, ibuprofen, flurbiprofen and nabumetone in an aerosol form comprising:
   a. heating a thin layer containing the drug, on a solid support, to produce a vapor of the drug, and
   b. providing an air flow through the vapor to form a condensation aerosol characterized by less than 10% drug degradation products by weight, and an MMAD of less than 5 microns.

5. The method according to claim 4, wherein the condensation aerosol is formed at a rate greater than $10^9$ particles per second.

6. The method according to claim 5, wherein the condensation aerosol is formed at a rate greater than $10^{10}$ particles per second.

7. The condensation aerosol according to claim 1, wherein the condensation aerosol is characterized by an MMAD of 0.1 to 5 microns.

8. The condensation aerosol according to claim 1, wherein the condensation aerosol is characterized by an MMAD of less than 3 microns.

9. The condensation aerosol according to claim 1, wherein the condensation aerosol is characterized by an MMAD of about 0.2 to 3 microns.

10. The condensation aerosol according to claim 1, wherein the condensation aerosol is characterized by less than 5% drug degradation products by weight.

11. The condensation aerosol according to claim 10, wherein the condensation aerosol is characterized by less than 2.5% drug degradation products by weight.

12. The condensation aerosol according to claim 1, wherein the solid support is a metal foil.

13. The condensation aerosol according to claim 1, wherein the drug is indomethacin.

14. The condensation aerosol according to claim 1, wherein the drug is ketoprofen.

15. The condensation aerosol according to claim 1, wherein the drug is celcoxib.

16. The condensation aerosol according to claim 1, wherein the drug is rofecoxib.

17. The condensation aerosol according to claim 1, wherein the drug is meclofenamic acid.

18. The condensation aerosol according to claim 1, wherein the drug is fenoprofen.

19. The condensation aerosol according to claim 1, wherein the drug is diflunisal.

20. The condensation aerosol according to claim 1, wherein the drug is tolfenamic acid.

21. The condensation aerosol according to claim 1, wherein the drug is naproxen.

22. The condensation aerosol according to claim 1, wherein the drug is ibuprofen.

23. The condensation aerosol according to claim 1, wherein the drug is flurbiprofen.

24. The condensation aerosol according to claim 1, wherein the drug is nabumetone.

25. The method according to claim 4, wherein the condensation aerosol is characterized by an MMAD of 0.1 to 5 microns.

26. The method according to claim 4, wherein the condensation aerosol is characterized by an MMAD of less than 3 microns.

27. The method according to claim 4, wherein the condensation aerosol is characterized by an MMAD of about 0.2 to 3 microns.

28. The method according to claim 4, wherein the condensation aerosol is characterized by less than 5% drug degradation products by weight.

29. The method according to claim 28, wherein the condensation aerosol is characterized by less than 2.5% drug degradation products by weight.

30. The method according to claim 4, wherein the solid support is a metal foil.

31. The method according to claim 4, wherein the drug is indomethacin.

32. The method according to claim 4, wherein the drug is ketoprofen.

33. The method according to claim 4, wherein the drug is celcoxib.

34. The method according to claim 4, wherein the drug is rofecoxib.

35. The method according to claim 4, wherein the drug is meclofenamic acid.

36. The method according to claim 4, wherein the drug is fenoprofen.

37. The method according to claim 4, wherein the drug is diflunisal.

38. The method according to claim 4, wherein the drug is tolfenamic acid.

39. The method according to claim 4, wherein the drug is naproxen.

40. The method according to claim 4, wherein the drug is ibuprofen.

41. The method according to claim 4, wherein the drug is flurbiprofen.

42. The method according to claim 4, wherein the drug is nabumetone.

43. A condensation aerosol for delivery of indomethacin, wherein the condensation aerosol is formed by heating a thin layer containing indomethacin, on a solid support, to produce a vapor of indomethacin, and condensing the vapor to form a condensation aerosol characterized by less than 5% indomethacin degradation products by weight, and an MMAD of about 0.2 to 3 microns.

44. A condensation aerosol for delivery of ketoprofen, wherein the condensation aerosol is formed by heating a thin layer containing ketoprofen, on a solid support, to produce a vapor of ketoprofen, and condensing the vapor to form a condensation aerosol characterized by less than 5% ketoprofen degradation products by weight, and an MMAD of about 0.2 to 3 microns.

45. A condensation aerosol for delivery of celcoxib, wherein the condensation aerosol is formed by heating a thin layer containing celcoxib, on a solid support, to produce a vapor of celcoxib, and condensing the vapor to form a condensation aerosol characterized by less than 5% celcoxib degradation products by weight, and an MMAD of about 0.2 to 3 microns.

46. A condensation aerosol for delivery of rofecoxib, wherein the condensation aerosol is formed by heating a thin layer containing rofecoxib, on a solid support, to produce a vapor of rofecoxib, and condensing the vapor to form a condensation aerosol characterized by less than 5% rofecoxib degradation products by weight, and an MMAD of about 0.2 to 3 microns.

47. A condensation aerosol for delivery of meclofenamic acid, wherein the condensation aerosol is formed by heating a thin layer containing meclofenamic acid, on a solid support, to produce a vapor of meclofenamic acid, and condensing the vapor to form a condensation aerosol characterized by less than 5% meclofenamic acid degradation products by weight, and an MMAD of about 0.2 to 3 microns.

48. A condensation aerosol for delivery of fenoprofen, wherein the condensation aerosol is formed by heating a thin layer containing fenoprofen, on a solid support, to produce a vapor of fenoprofen, and condensing the vapor to form a condensation aerosol characterized by less than 5% fenoprofen degradation products by weight, and an MMAD of 0.2 to 3 microns.

49. A condensation aerosol for delivery of diflunisal, wherein the condensation aerosol is formed by heating a thin layer containing diflunisal, on a solid support, to produce a vapor of diflunisal, and condensing the vapor to form a condensation aerosol characterized by less than 5% diflunisal degradation products by weight, and an MMAD of about 0.2 to 3 microns.

50. A condensation aerosol for delivery of tolfenamic acid, wherein the condensation aerosol is formed by heating a thin layer containing tolfenamic acid, on a solid support, to produce a vapor of tolfenamic acid, and condensing the vapor to form a condensation aerosol characterized by less than 5% tolfenamic acid degradation products by weight, and an MMAD of about 0.2 to 3 microns.

51. A condensation aerosol for delivery of naproxen, wherein the condensation aerosol is formed by heating a thin layer containing naproxen, on a solid support, to produce a vapor of naproxen, and condensing the vapor to form a condensation aerosol characterized by less than 5% naproxen degradation products by weight, and an MMAD of about 0.2 to 3 microns.

52. A condensation aerosol for delivery of ibuprofen, wherein the condensation aerosol is formed by heating a thin layer containing ibuprofen, on a solid support, to produce a vapor of ibuprofen, and condensing the vapor to form a condensation aerosol characterized by less than 5% ibuprofen degradation products by weight, and an MMAD of about 0.2 to 3 microns.

53. A condensation aerosol for delivery of flurbiprofen, wherein the condensation aerosol is formed by heating a thin layer containing flurbiprofen, on a solid support, to produce a vapor of flurbiprofen, and condensing the vapor to form a condensation aerosol characterized by less than 5% flurbiprofen degradation products by weight, and an MMAD of about 0.2 to 3 microns.

54. A condensation aerosol for delivery of nabumetone, wherein the condensation aerosol is formed by heating a thin layer containing nabumetone, on a solid support, to produce a vapor of nabumetone, and condensing the vapor to form a condensation aerosol characterized by less than 5% nabumetone degradation products by weight, and an MMAD of about 0.2 to 3 microns.

55. A method of producing indomethacin in an aerosol form comprising:
  a. heating a thin layer containing indomethacin, on a solid support, to produce a vapor of indomethacin, and
  b. providing an air flow through the vapor to form a condensation aerosol characterized by less than 5% indomethacin degradation products by weight, and an MMAD of about 0.2 to 3 microns.

56. A method of producing ketoprofen in an aerosol form comprising:
  a. heating a thin layer containing ketoprofen, on a solid support, to produce a vapor of ketoprofen, and
  b. providing an air flow through the vapor to form a condensation aerosol characterized by less than 5% ketoprofen degradation products by weight, and an MMAD of about 0.2 to 3 microns.

57. A method of producing celcoxib in an aerosol form comprising:
  a. heating a thin layer containing celcoxib, on a solid support, to produce a vapor of celcoxib, and
  b. providing an air flow through the vapor to form a condensation aerosol characterized by less than 5% celcoxib degradation products by weight, and an MMAD of about 0.2 to 3 microns.

58. A method of producing rofecoxib in an aerosol form comprising:
  a. heating a thin layer containing rofecoxib, on a solid support, to produce a vapor of rofecoxib, and
  b. providing an air flow through the vapor to form a condensation aerosol characterized by less than 5% rofecoxib degradation products by weight, and an MMAD of about 0.2 to 3 microns.

59. A method of producing meclofenamic acid in an aerosol form comprising:
  a. heating a thin layer containing meclofenamic acid, on a solid support, to produce a vapor of meclofenamic acid, and
  b. providing an air flow through the vapor to form a condensation aerosol characterized by less than 5% meclofenamic acid degradation products by weight, and an MMAD of about 0.2 to 3 microns.

60. A method of producing fenoprofen in an aerosol form comprising:
  a. heating a thin layer containing fenoprofen, on a solid support, to produce a vapor of fenoprofen, and
  b. providing an air flow through the vapor to form a condensation aerosol characterized by less than 5% fenoprofen degradation products by weight, and an MMAD of about 0.2 to 3 microns.

61. A method of producing diflunisal in an aerosol form comprising:
  a. heating a thin layer containing diflunisal, on a solid support, to produce a vapor of diflunisal, and
  b. providing an air flow through the vapor to form a condensation aerosol characterized by less than 5% diflunisal degradation products by weight, and an MMAD of about 0.2 to 3 microns.

62. A method of producing tolfenamic acid in an aerosol form comprising:
  a. heating a thin layer containing tolfenamic acid, on a solid support, to produce a vapor of tolfenamic acid, and
  b. providing an air flow through the vapor to form a condensation aerosol characterized by less than 5% tolfenamic acid degradation products by weight, and an MMAD of about 0.2 to 3 microns.

63. A method of producing naproxen in an aerosol form comprising:
  a. heating a thin layer containing naproxen, on a solid support, to produce a vapor of naproxen, and
  b. providing an air flow through the vapor to form a condensation aerosol characterized by less than 5% naproxen degradation products by weight, and an MMAD of about 0.2 to 3 microns.

64. A method of producing ibuprofen in an aerosol form comprising:
  a. heating a thin layer containing ibuprofen, on a solid support, to produce a vapor of ibuprofen, and
  b. providing an air flow through the vapor to form a condensation aerosol characterized by less than 5% ibuprofen degradation products by weight, and an MMAD of about 0.2 to 3 microns.

65. A method of producing flurbiprofen in an aerosol form comprising:
  a. heating a thin layer containing flurbiprofen, on a solid support, to produce a vapor of flurbiprofen, and
  b. providing an air flow through the vapor to form a condensation aerosol characterized by less than 5% flurbiprofen degradation products by weight, and an MMAD of about 0.2 to 3 microns.

66. A method of producing nabumetone in an aerosol form comprising:
  a. heating a thin layer containing nabumetone, on a solid support, to produce a vapor of nabumetone, and
  b. providing an air flow through the vapor to form a condensation aerosol characterized by less than 5% nabumetone degradation products by weight, and an MMAD of about 0.2 to 3 microns.

\* \* \* \* \*